US012465333B2

(12) United States Patent
Mezzoli et al.

(10) Patent No.: US 12,465,333 B2
(45) Date of Patent: Nov. 11, 2025

(54) COLLECTOR FOR LIQUIDS

(71) Applicants: Giorgio Mezzoli, Lugo (IT); Maria Rani, Lugo (IT)

(72) Inventors: Giorgio Mezzoli, Lugo (IT); Maria Rani, Lugo (IT)

( * ) Notice: Subject to any disclaimer, the term of this patent is extended or adjusted under 35 U.S.C. 154(b) by 465 days.

(21) Appl. No.: 18/019,950

(22) PCT Filed: Nov. 13, 2020

(86) PCT No.: PCT/IB2020/060698
§ 371 (c)(1),
(2) Date: Feb. 6, 2023

(87) PCT Pub. No.: WO2022/029480
PCT Pub. Date: Feb. 10, 2022

(65) Prior Publication Data

US 2023/0293156 A1 Sep. 21, 2023

(30) Foreign Application Priority Data

Aug. 7, 2020 (IT) ........................ 102020000019663

(51) Int. Cl.
*A61B 10/00* (2006.01)
*A61M 3/02* (2006.01)

(52) U.S. Cl.
CPC ....... *A61B 10/0051* (2013.01); *A61M 3/0287* (2013.01); *A61M 2202/206* (2013.01); *A61M 2210/0618* (2013.01)

(58) Field of Classification Search
CPC ............ A61B 10/0051; A61B 10/0045; A61B 10/0096; A61B 10/02; A61M 3/0287;
(Continued)

(56) References Cited

U.S. PATENT DOCUMENTS

| | | | |
|---|---|---|---|
| 2009/0108097 | A1 | 4/2009 | Lee et al. |
| 2010/0152653 | A1 | 6/2010 | Hoke et al. |
| 2017/0028144 | A1 | 2/2017 | Flickinger |

FOREIGN PATENT DOCUMENTS

| | | |
|---|---|---|
| CN | 2474138 | 1/2002 |
| CN | 208017763 | 10/2018 |

(Continued)

OTHER PUBLICATIONS

International Search Report and Written Opinion in corresponding International Patent Application No. PCT/IB2020/060698, mailed Apr. 23, 2021 (9 pages).

(Continued)

*Primary Examiner* — Eric F Winakur
*Assistant Examiner* — Hy Khanh Doan
(74) *Attorney, Agent, or Firm* — Leason Ellis LLP

(57) ABSTRACT

A collector (1) for liquids provided with a first funnel-shaped body (10) delimited at the top by an annular edge (12) and provided at the bottom with an outlet (11) for liquids and with coupling means (100) for removable collection members (102) of the liquids from the outlet (11); a first front wall (120) and a second rear wall (122) carried in a hydraulically sealed manner by the annular edge (12) between two sides (124) of the first body (10) and mutually facing one another; the second wall (122) being delimited at the top by a concave curved segment (1220) shaped for shape coupling, in use, with an anatomic facial portion arranged between a user's top lip and nose.

13 Claims, 14 Drawing Sheets

(58) Field of Classification Search
CPC .......... A61M 3/0262; A61M 2202/206; A61M 2202/20; A61M 2210/0618; A61M 1/69; A61M 11/007; A61H 2201/1604; A61H 2205/023; A61H 35/04
See application file for complete search history.

(56) References Cited

FOREIGN PATENT DOCUMENTS

| | | |
|---|---|---|
| WO | 2010126586 | 11/2010 |
| WO | 2019091159 | 5/2019 |

OTHER PUBLICATIONS

International Preliminary Report on Patentability in PCT Application No. PCT/IB2020/060698, mailed Jul. 19, 2022 (5 pages).

COLLECTOR FOR LIQUIDS

CROSS-REFERENCE TO RELATED PATENT APPLICATIONS

This Patent Application is a U.S. National Phase Application under 35 U.S.C. § 371 of International Patent Application No. PCT/IB2020/060698, filed on Nov. 13, 2020, which claims priority from Italian Patent Application No. 102020000019663, filed on Aug. 7, 2020, all of which are incorporated by reference, as if expressly set forth in their respective entireties.

DESCRIPTION

The present invention concerns a collector for liquids. In particular, the present invention refers to a collector for liquids pre-arranged to support a liquid delivery device for performing nasal washes. In further detail, the present invention refers to a collector for liquids pre-arranged to support a liquid delivery device for performing nasal washes and for collecting the nasal secretion mixed with the liquid delivered.

DESCRIPTION OF THE STATE OF THE ART

The diagnosis of infections of the upper respiratory tract can be performed by analysing the nasal secretion collected from the nasopharyngeal or olfactory area using a small stick provided with a sterile cotton swab at a respective end. The stick must be flexible and, operatively, the swab is inserted in a nostril and pushed horizontally to reach the nasopharyngeal area or pushed upwards to reach the olfactory area until encountering resistance. Having ascertained that the resistance is determined by the swab reaching the area in which the sample is to be taken, the swab is gently rotated to locally remove biological material consisting of the nasal secretion. At this point, the swab is extracted and the cotton end is inserted in a sterile container for conservation and transport to a laboratory, where the biological material removed is analysed, once it has undergone microbiological culture or other tests to isolate and identify the pathogen.

From the above description it is evidently highly recommended for the swab to be carried out by an expert operator, with a good knowledge of nasal anatomy and the ability to identify the anatomical conformation of the nasal cavity of the patient to be examined. This enables the operator to decide whether it is preferable to take the nasal secretion from the nasopharyngeal or olfactory area, in order to preserve the mucosa of the nasal area of the individual to be examined and with a reasonable certainty of the sample being taken in an effective manner.

In emergency situations, in which the number of individuals to be examined is particularly high and well exceeds the number of expert operators for carrying out the swab in the nasopharyngeal or olfactory area, for example, but not limited to, in a full-blown pandemic, there is evidently the risk, on the one hand, of the number of samples being too low to provide a rapid reliable photograph of the infection levels, and on the other hand, of the information resulting from analysis of the swabs not faithfully representing the infection situation. In both cases the resulting situation is highly unsatisfactory, since public health is at stake. Furthermore, it is important to consider the aspect of operator safety if the swab is to be carried out on individuals who already present symptoms of infection. In these cases, the operator must necessarily wear personal protective clothing and equipment able to fully cover his/her body; on the other hand, considering that said clothing/devices are of the disposable type, they produce a considerable increase in the cost of the activities correlated with testing and checking of the operators, in addition to being subject to supply chain risk.

Examples of conventional collectors are known from WO 2019/091159 A1, US 2009/108097 A1, WO 2010/126586 A1, US 2017/028144 A1, US 2010/152653 A1, CN 208 017 763 U, CN 2 474 138 Y.

In view of the situation described above, a device that is practical to use and has a limited cost would be desirable, allowing biological samples to be taken, autonomously and effectively, from the nasopharyngeal or olfactory area, therefore without involving expert operators, with the result of eliminating the risk of infection of the health care workers involved in the analysis. It is evident that the use of said devices, in addition to limiting and, if possible, overcoming the typical drawbacks of the known art illustrated above, allows new operating protocols to be defined for the sampling of nasopharyngeal/olfactory nasal secretions of numerous groups of people to be analysed in complete safety and with a high degree of reliability. In particular, it allows the patients to self-collect nasal secretions mixed with washing liquid, thus excluding the risk of third-party infection and errors.

SUMMARY OF THE PRESENT INVENTION

The present invention concerns a collector for liquids. In particular, the present invention refers to a collector for liquids pre-arranged to support a liquid delivery device for carrying out nasal washes. In further detail, the present invention refers to a collector for liquids pre-arranged to support a liquid delivery device for carrying out nasal washes and for collecting the nasal secretion mixed with the liquid delivered.

The above drawbacks are solved by the present invention according to at least one of the following claims.

According to some embodiments of the present invention, a collector for liquids is produced provided with a first funnel-shaped body delimited at the top by an annular edge and provided at the bottom with an outlet for said liquids and coupling means for the removable collection members for collecting said liquids from said outlet; characterized in that it comprises a first front wall and a second rear wall carried in a hydraulically sealed manner by said annular edge between two sides of said first body and mutually facing each other; said second wall being delimited at the top by a concave curved segment shaped for shape coupling, in use, with an anatomic facial portion arranged between the upper lip and nose of a user.

According to an embodiment as described above, said first wall and said second wall are symmetrically shaped relative to a centreline plane that transversely cuts said first body; said curved segment being laterally delimited by two raised angle portions arranged symmetrically to laterally delimit the nostrils of said nose.

According to an embodiment as described above, at least one interface is provided elongated in a given direction oriented in a given manner relative to said centreline plane and pre-arranged to house supply means designed to distribute the liquid in a direction opposite to said outlet between said first wall and said second wall through a nasal nozzle.

According to an embodiment as described above, said first wall and said second wall are separated in at least a first side of said two sides creating a first opening above said first body; a said first interface being carried by said first side transversely to said centreline plane facing said first body through said first opening.

According to an embodiment as described above, said first interface has a retention element for retaining said liquid delivery means at the corresponding said first side.

According to an embodiment as described above, said liquid supply means comprise a syringe provided with a said nasal nozzle carried longitudinally or transversely by said syringe; said retention element comprising an at least partially cylindrical projecting part with angular width greater than 180° and arranged at the connection between said first interface and said first side.

According to an embodiment as described above, said first wall extends from said annular edge by a greater extent than said second wall.

According to an embodiment as described above, said first wall carries at the top a tapered cover member shaped for containing a nasal pyramid starting from a relative root.

According to an embodiment as described above, said first wall and said second wall are separated in a second side of said two sides, creating a second opening identical or geometrically similar and opposite to said first opening; a said second interface carried by said second side aligned with said first interface and sized in an identical or geometrically similar manner.

According to an embodiment as described above, said first wall and said second wall are connected to the sides of said first body by respective opposite walls shaped symmetrically relative to said centreline plane.

According to an embodiment as described above, said first wall and said second wall have respective concavities facing, from opposite or same sides, said outlet.

According to an embodiment as described above, said coupling means comprise in combination or alternatively a first cylindrical portion that peripherally delimits said outlet and terminates with a first hooking portion, shaped to couple in a hydraulically sealed manner with an upper edge of a collection vial for a liquid to be analysed, and a second cylindrical hooking portion coaxial to said outlet shaped to house a hydraulically sealed test tube.

According to an embodiment as described above, a said third interface is carried at the bottom by said first body alongside said outlet, extends parallel to said centreline plane and transversely to said annular edge and being pre-arranged to house said syringe with said outlet nozzle that protrudes inside said first body to support said nasal nozzle directly or through an extension carried by said third interface inside said first body.

According to an embodiment as described above, a said fourth interface comprises a housing member carried at the bottom by said first visible body; said housing member being pre-arranged to house a two-way hydraulic selector provided with a first and a second duct aligned with each other and a duct transversal to the other two, in addition to a switching tap; said first aligned duct engaging, in use, said outlet and carrying said nasal nozzle inside the first body; said second aligned duct engaging a test tube or vial selectively supported at the bottom by said housing member; said transverse duct being engaged by an outlet nozzle of said syringe; said tap being designed to selectively determine the connection between said first aligned duct and said transverse duct and the connection between said first aligned duct and said second aligned duct.

BRIEF DESCRIPTION OF THE FIGURES

Further characteristics and advantages of collectors produced by applying the teachings of the present invention will appear clearer from the following description, with reference to the attached figures that illustrate at least a non-limiting embodiment example thereof, wherein identical or corresponding parts of the collector are identified by the same reference numbers. In particular.

DETAILED DISCLOSURE OF THE PRESENT INVENTION

Before describing in detail the preferred embodiments of the present invention or details thereof, it is useful to specify that the relative scope is not limited to the particular embodiments described below. The disclosure and description in the present document are illustrative and explanatory of one or more embodiments and variations currently preferred, and it will be clear to persons skilled in the art that various changes can be made in the design, in the organization, in the order of operation, in the means of operation, in the structures of the equipment and position, and in the methodology and use of mechanical equivalents without departing from the spirit of the invention.

Furthermore, it should be understood that the attached figures have the purpose of clearly illustrating and disclosing currently preferred embodiments to a person skilled in the art, but they are not drawings that illustrate how said embodiments should be executed in reality or real representations of final products; on the contrary, said figures can comprise conceptual views simplified to facilitate comprehension or allow for an easier and quicker explanation. Furthermore, the relative dimensions and arrangement of the components can differ from those shown and still function within the spirit of the invention.

Figure 1:
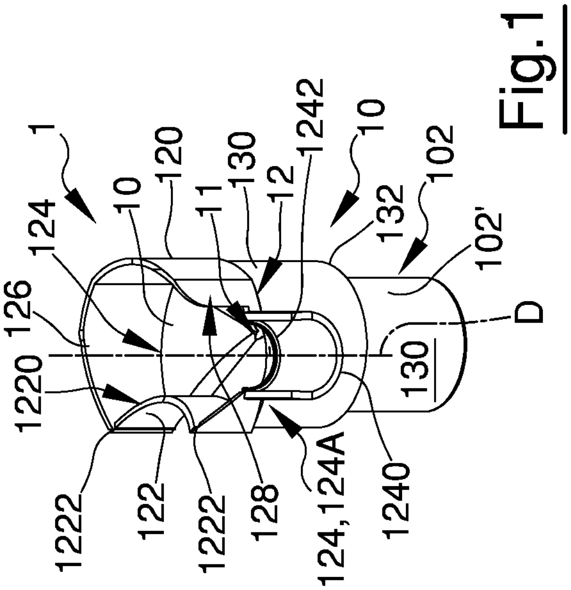
FIG. 1 is a first three-dimensional schematic view of a preferred embodiment of the present invention.

Various indications such as "upper", "lower", "left-hand", "right-hand", "front", "rear" and so on refer only to the explanation in combination with the drawings and the components can be oriented differently, for example during transport and production, and during operation. Since many different and distinct embodiments can be produced in the context of the concepts taught here, and since multiple modifications can be made to the embodiments described here, the details provided below must be interpreted as illustrative and non-limiting with regard to the spirit of the invention. In FIG. 1, the number 1 indicates, overall, a collector for liquids provided with a first concave body 10 shaped symmetrically like a funnel relative to a vertical centreline plane MT that cuts through it transversely, which can be seen better in FIG. 3. Said first body 10 laterally delimits a volume with a section decreasing from an annular edge 12 and is provided at the bottom with an outlet 11 provided with a hole for passage of the liquids arranged in the lowest point of the first body 10, in a preferably central position, but not limited to said position.

Figure 2:
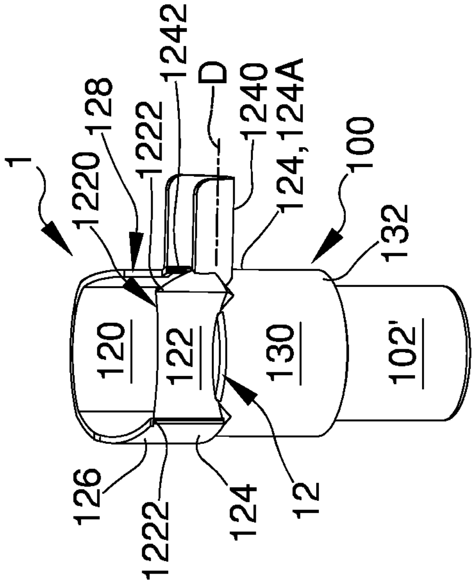
FIG. 2 is a second three-dimensional schematic view of FIG. 1.
Figure 4:
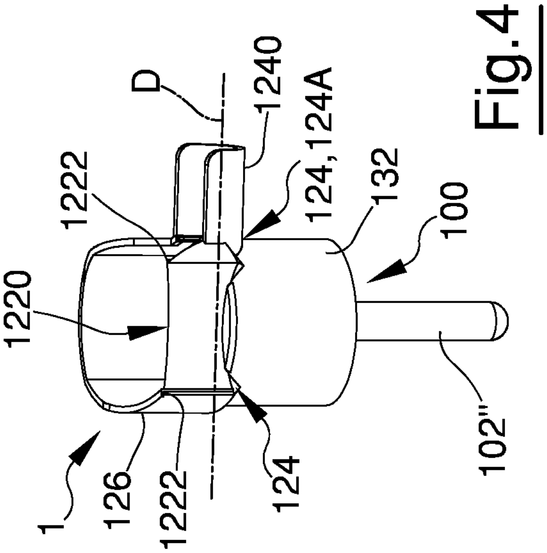
FIG. 4 is a front elevation view of FIG. 1.
Figure 6:
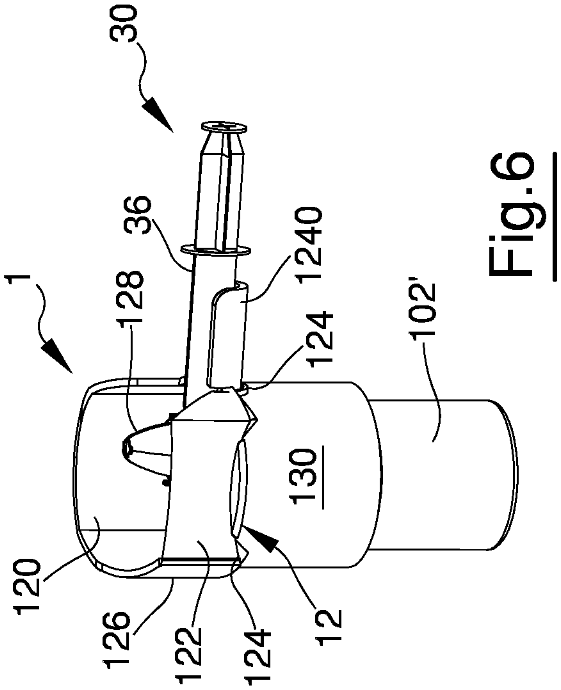
FIGS. 6-9 show FIG. 1 in different operating situations.
Figure 8:
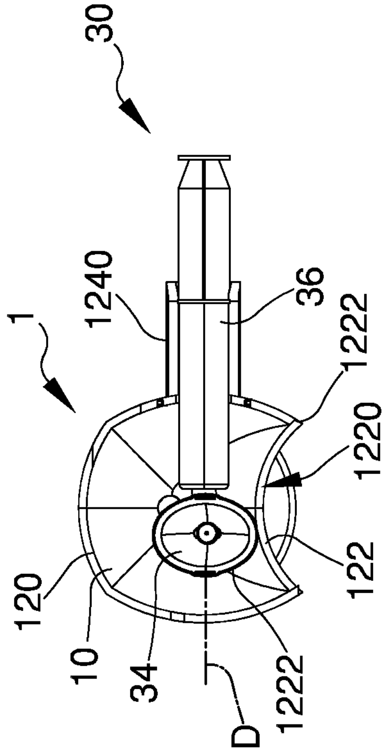
Figure 5:
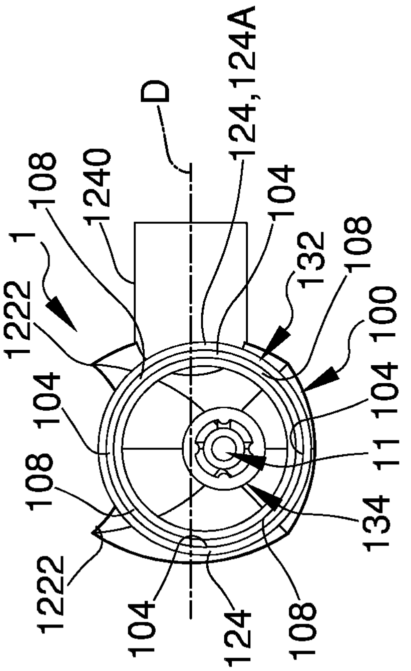
FIG. 5 is a view from below of FIG. 1.
Figure 7:
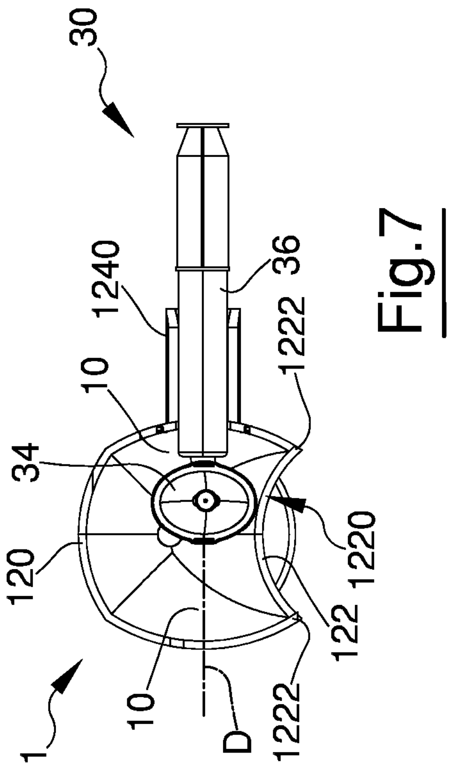

With particular reference to FIGS. 1, 2 and 5, the collector 1 has at the bottom coupling members 100 which can be used to selectively connect the removable collection members 102 to the first body 10, in particular below the outlet 11 to receive through the latter liquids from the first body 10. Said coupling members 100 comprise, in combination or alternatively, a first cylindrical portion 130 which is positioned below the annular edge 12, peripherally delimits the outlet 11 and terminates with a first hooking portion 132 provided with a cylindrical seat that extends for the respective length, the lower edge of which is shaped to couple in a hydraulically sealed manner with an upper edge of a vial 102' for collecting liquids to be analysed (FIGS. 1 and 2), and/or a second hooking portion 134 coaxial with the outlet 11 and provided with a cylindrical seat which extends for the respective length, the lower edge of which is shaped to house in a hydraulically sealed manner a test tube 102" (FIG. 4) through a respective upper edge. For the sake of practicality, the embodiment of the collector 1 shown in FIGS. 1-5 has both the cylindrical portion 130 and the second hooking portion 134 for the test tube 102", without limiting the scope of the present invention to said embodiment.

With particular reference to FIG. 5, the cylindrical seats of the first hooking portion 132 and of the second hooking portion 134 have at least one longitudinal rib 104, the cross-section of which is semi-cylindrical and which, at the bottom, has a respective rounded end, the function of which is to facilitate insertion of the vial 102' or the test tube 102", respectively, in order to improve the capacity to retain the vials 102' and the capacity to retain the test tubes 102". Furthermore, the cylindrical seats of the first hooking portion 132 and of the second hooking portion 134 have at the bottom at least one axial abutment 108 for the edges of the vials 102' and the test tubes 102" respectively. It should be noted that the ribs 104 and the abutments 108 have the function of maintaining the inner mantle of the vials 102' and the test tubes 102" and, respectively, the free edges of the openings of the vials 102' and of the test tubes 102" detached from the bottoms of the cylindrical seats. This characteristic allows discharge of the air contained in the vials 102' and in the test tubes 102" which would otherwise prevent filling of said containers with liquid mixed with nasal secretion received from the first concave body 10 through the outlet 11.

The first body 10 furthermore has two lateral sides 124 and the collector 1 comprises a first front wall 120 and a second rear wall 122 symmetrically shaped relative to the centreline plane MT and carried by the annular edge 12 in a hydraulically sealed manner mutually facing each other between the two sides 124. The first wall 120 and the second wall 122 are connected in one side 124 by a lateral wall 126.

Figure 3:
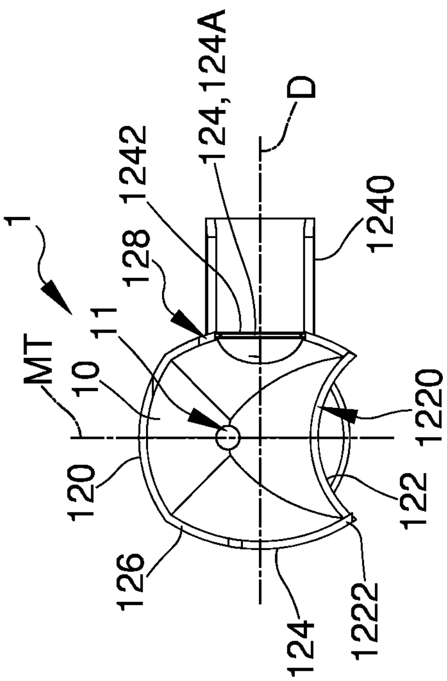
FIG. 3 is a plan view of FIG. 1.

With particular reference to FIGS. 1, 3 and 5 the second wall 122 is delimited at the top by a concave curved segment 1220 which is shaped for shape coupling, in use, with a facial anatomic portion arranged between the upper lip and nose of a user. Furthermore, the first wall 120 extends from the annular edge 12 to a greater extent than the second wall 122 and the curved segment 1220 is laterally delimited by two symmetrically shaped angle portions 1222 which, in use, are designed to laterally delimit the nostrils of said nose. Said angle portions are raised relative to a central portion of the second wall 122 and are, preferably but not exclusively, cuspate although they could be rounded without departing from the scope of the present invention.

With reference to FIGS. 1-5, the collector 1 comprises, facing the lateral wall 126, a first interface 1240 elongated according to a given direction D transverse to the centreline plane MT. Said first interface 1240 is shaped to house supply members 30 (FIGS. 6-9) designed to distribute the liquid between the first wall 120 and the second wall 122, either in a nebulized or liquid jet form, in a direction opposite to the outlet 11, therefore upwards, through a dispenser, preferably but not exclusively a nasal nozzle 34, specifically shaped to adhere in a hydraulically sealed manner to the respective nasal vestibule, by simply exerting a slight pressure transversely to the latter. In the attached figures said nozzle is illustrated by a dome-shaped body, but said embodiment shape is purely an example and is not intended to limit the scope of the present invention.

In particular, the supply members 30 comprise a syringe 36 which is, in turn, provided with the nasal nozzle 34, which is carried longitudinally or transversely by an outlet nozzle, known and not illustrated, of the syringe 36 according to requirements for carrying out nasal washes with a given liquid, either in a nebulized or liquid jet form.

With reference to FIG. 1 the first wall 120 and the second wall 122 are separated into at least a first side 124A of the two sides 124 creating a first opening 128 above the first body 10. In particular, the first interface 1240 is carried by the first side 124A transversely to the centreline plane MT facing the first body 10 through the first opening 128.

The first interface 1240 has a retention element 1242 for retaining the liquid delivery members 30, and in particular the syringe 36, at the relative first opening 128 on the side of the first side 124. More specifically, the retention element 1242 consists of an at least partially cylindrical projecting part 1242 (which for the sake of practicality is indicated by the same reference number) with angular width greater than 180° arranged at the connection between the first interface 1240 and the first side 124 to retain the syringe 36 in any longitudinal position determined as required by the user.

The use of the collector 1 described above is easy to understand and does not require any further explanation. However, with particular reference to FIGS. 4-9, it is useful to specify that once a vial 102' (FIGS. 5-9) for analysis has been coupled to the first hooking portion 132 of the internally hollow cylindrical portion 130, or a test tube 102" (FIG. 4) has been coupled to the second hooking portion 134 and a syringe 36 has been positioned filled with washing liquid and provided with the respective nasal nozzle 34 inside the first interface 1240, a user can grip the collector 1 by the cylindrical portion 130, move said collector 1 closer with the second wall 122 between his/her upper lip and nose, slide the syringe 36 longitudinally in the direction D until it is positioned with the nasal nozzle 34 facing one of the two nostrils, to perform at least a first washing part of the nasal cavity. At this point the syringe 36 is blocked longitudinally and transversely by the projecting part 1242 and, before proceeding, the collector 1 must be further pressed upwards until the nasal nozzle 34 engages in a hydraulically sealed manner the nasal vestibule of the selected nostril, so as to maximize the probability of the liquid in the syringe 36 being delivered totally inside the nasal cavity. At this point, the second wall 122 must be pushed gently against the skin between the upper lip and the nasal pyramid and the head inclined forward, maintaining the collector 1 with the edge 12 of the first body 10 substantially horizontal so as to maximize the probability of the liquid in the syringe 36, once discharged from one of the two nostrils, or from both, remaining inside the first body 10 without even a splash of the liquid being able to leak out, during the discharge phase, above the first wall 120 or from the opening 128 obtained in the first side 124. If any liquid splashes onto the first or second wall 120/122 or onto the skin between the upper lip and nasal pyramid of the user, it would drop back into the first body 10 by gravity, without requiring any external intervention.

At this point the piston of the syringe 36 can be operated, emptying it partially or completely of the liquid contained and, as described above, delivered inside the nasal cavity through the chosen nasal vestibule.

Figure 9:
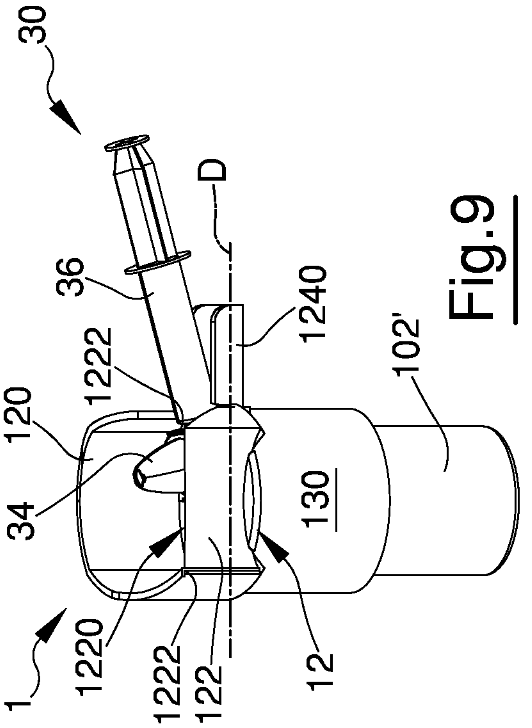

It is evident that if the volume of liquid contained in the syringe 36 is lower than the volume of the nasal cavity, all the liquid delivered to the nasal cavity will remain inside said cavity until complete emptying of the syringe 36 and for as long as the nasal nozzle 34 is kept in a hydraulically sealed manner inside the chosen nasal vestibule. If, on the other hand, the volume of liquid contained in the syringe 36 is greater than the volume of the nasal cavity, when the nasal cavity is completely filled, the excess liquid will begin to flow spontaneously through the nasopharynx to the other nostril and from here inside the first body 10; from here, it then flows inside the vial 102' or the test tube 102" through the outlet 11. In both cases, but above all in the case of the volume of liquid contained in the syringe 36 being lower than the volume of the nasal cavity, discharge of the liquid delivered and the nasal secretion removed by the latter from the inside of the nasal cavity is permitted only after removing the nasal nozzle 34 from the nasal vestibule engaged in a hydraulically sealed manner. Considering that the minimum movement of the nasal nozzle 34 relative to the nostril engaged could cause outflow of the liquid contained in the corresponding nasal cavity, to be reasonably certain that the washing liquid flows completely in the first body 10, and from there freely by gravity into the vial or test tube 102" through the outlet 11, firstly the user must keep his/her head in a slightly forward inclined position and leave the collector 1 with the edge 12 of the first body 10 horizontal, with the curved segment 1220 of the second wall 122 in contact in a hydraulically sealed manner with the skin between the nose and the upper lip. Since it is not possible to slide the syringe 36 to free the nasal nozzle 34 from the nasal vestibule, to avoid damaging it, the user can use the projecting part 1242 arranged at the connection of the first interface 1240 as if it were a hinge point for the syringe 36. In fact, said projecting part 1242 exerts a circumferential pressure on a given portion of the syringe 36, arranged between the first interface 1240 and the first body 10, allowing it to be hinged once a rotation as in FIG. 9 is exerted on the syringe, in order to cause the nasal nozzle 34 to leave the corresponding nasal vestibule.

As already said, with minimum movement of the nasal nozzle 34 from the operating position inside a nostril to a lowered position towards the outlet 11, the nasal secretion will flow out mixed with the liquid contained in the nasal cavity and will then be collected in the vial 102' or in the test tube 102", without a drop of said mixture being lost. The first wall 120, always kept by the user positioned in front of his/her nose, will prevent any drops of liquid coming out of the first body 10, with the risk of spraying the surrounding areas and persons who are knowingly or unknowingly near the user performing the nasal wash.

From the above description, it can be seen that the collector 1 is particularly useful whenever a nasal wash has to be performed by the user on his/her own and, considering that the washing liquid will always contain nasal secretion, if the collector 1 were made of plastic or pressed cardboard in order to be disposable, it would be particularly suitable for carrying out nasal washes also in persons with infectious diseases, for example but not exclusively coronavirus "SARS—COVID 19", for treatment or to collect the nasal secretion removed from the washing liquid in order to analyse it. Evidently using the collector 1 in this way would make it possible to collect nasal secretion from any part of the nasal cavity, and check for the presence of virus particles in any position of the nasal cavity/ies without the need to involve operators. In fact, once one of the two nasal cavities has been washed and the nasal nozzle 34 has been removed from the corresponding nostril, the user can raise his/her head slightly to free the nasal nozzle 34 and, therefore, leave the syringe 36 free to slide until the nasal nozzle 34 faces the nasal vestibule of the other nostril and complete the washing operation as described above. It should be highlighted that the sampling of nasal secretion by means of the collector 1 is particularly inexpensive.

Lastly it is clear that modifications and variations can be made to the collector 1 described and illustrated here without departing from the scope of the present invention.

Figure 10:
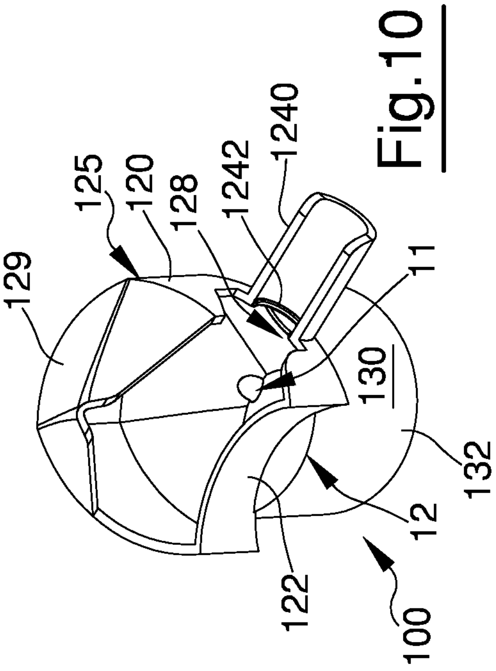
FIG. 10 is a three-dimensional schematic view of a second preferred embodiment of FIG. 1.
Figure 11:
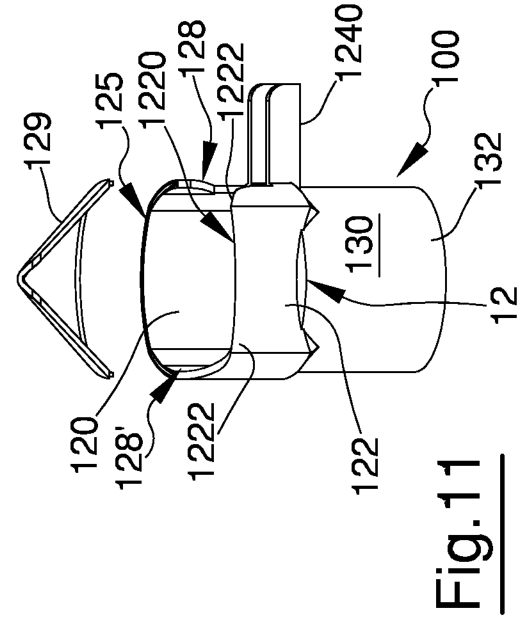
FIG. 11 is a front elevation and exploded view on a reduced scale of FIG. 10.

For example, to maximize safety of use of the collector 1 and prevent the liquid particles from flowing out at the top over the first wall 120, with particular reference to FIGS. 10 and 11 said wall could be modified with the addition of a tapered cover member 129 shaped to contain a nasal pyramid from a relative root to the respective upper edge BS. Naturally, said cover member 129 could be snap-connectable to the first wall 120 at a respective upper edge 125.

Figure 12:
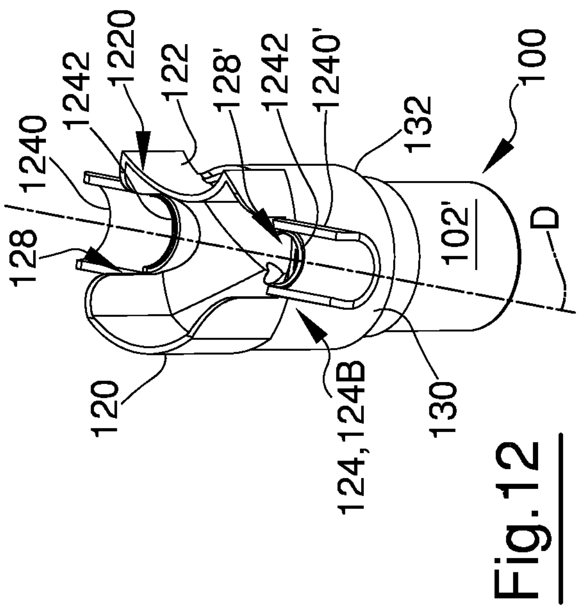
FIG. 12 is a three-dimensional schematic view of a third preferred embodiment of FIG. 1.
Figure 13:
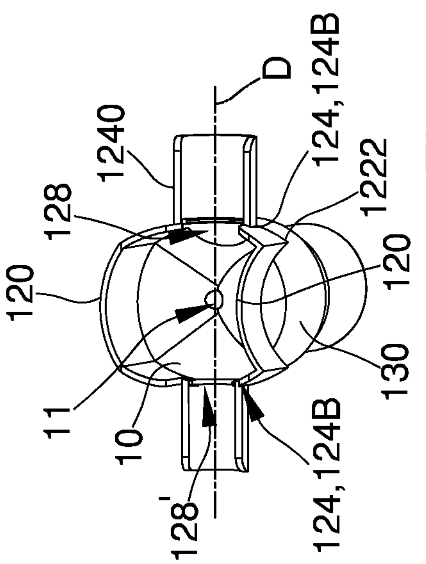
FIG. 13 is a plan view of FIG. 12.

With reference to FIGS. 12 and 13, a further embodiment of the collector 1 is shown designed to perform nasal washing using a syringe 36 with volume more suited to the volume of the nasal cavity of the user to be treated, but having two syringes with different volumes. In this case the collector 1 has a second interface 1240' aligned with the first interface 1240 and sized differently but geometrically similar, given the geometric configuration of syringes with different volumes. This structural characteristic of the collector 1 of FIGS. 12 and 13 allows the same collector 1 to be set up with two syringes 36 of different sizes to treat patients with nasal cavities of different volumes without having to “classify” the patients in advance based on said characteristic before carrying out the treatment on each of them. Said second interface 1240 is carried by a second side 124B of the two sides 124, where the first wall 120 is separated from the second wall 122 through a second opening 128' identical or geometrically similar to the first opening 128, taking account of the dimensions of the second interface 1240. In addition, it is useful to highlight that the collector 1 described with reference to FIGS. 12 and 13 has coupling members 100 identical to those of the collector 1 of FIGS. 1-9.

Figure 14:
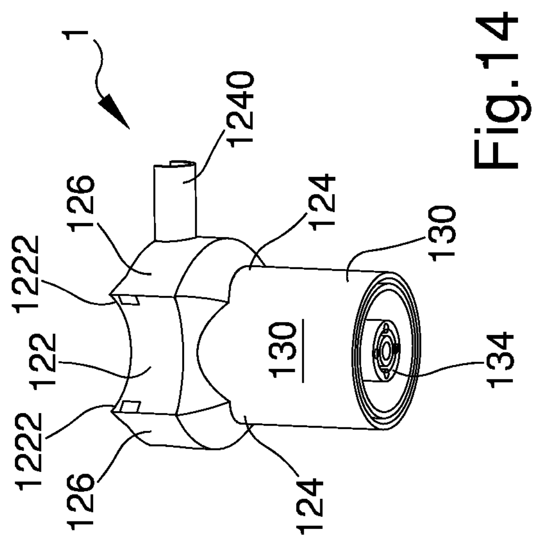
FIG. 14 is a three-dimensional schematic view of a fourth preferred embodiment of FIG. 1.
Figure 15:
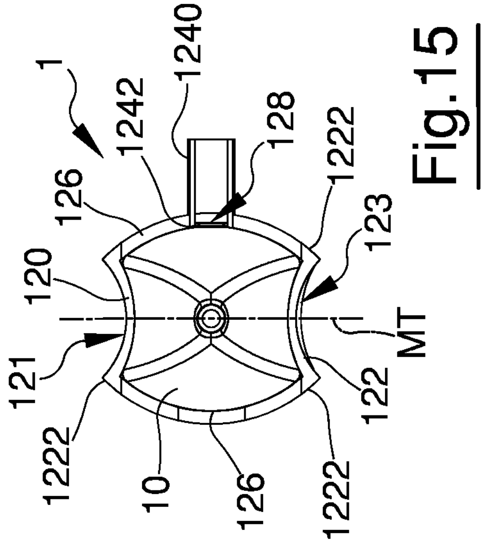
FIG. 15 is a plan view of FIG. 14.
Figure 16:
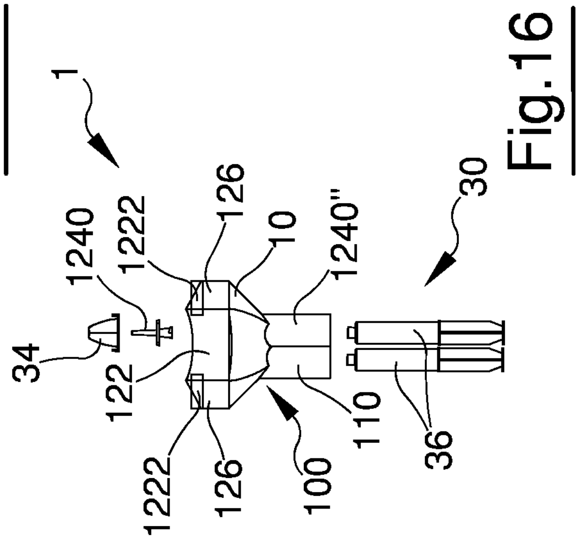
FIG. 16 is an exploded view in side elevation of a fifth preferred embodiment of FIG. 1 in a first operating condition.

With reference to the collector 1 shown in FIGS. 14 and 15, the first wall 120 and the second wall 122 of the collector 1 are connected to the sides 124 by a lateral wall 126 as in the case of the collector 1 of FIGS. 1-9. However, in this case, the first wall 120 and the second wall 122 are geometrically identical, shaped symmetrically relative to the centreline plane MT of the first body 10 and therefore identical also in terms of height. In addition, the first wall 120 and the second wall 122 have respective identical concavities 121 and 123 facing opposite sides (towards the outside) relative to the outlet 11. Therefore, each of the first wall 120 and second wall 122 is delimited by a curved segment which for the sake of practicality is numbered as 1220 like the concave segment 1220 of the collector 1 of FIGS. 1-9 and, in turn, is analogously delimited laterally by the angle portions 1222, also identical geometrically and dimensionally. It may be useful to specify that the first wall 120 and the second wall 122 are separated on the side opposite the lateral wall 126 by the opening 128 and that there is an interface geometrically identical to the first interface 1240 which is therefore numbered in FIGS. 14 and 15 with the same reference number as the one used in FIGS. 1-9. Also in this case the first interface 1240 is provided with the projecting part 1242. Lastly, the collector 1 of FIGS. 14 and 15 has coupling members 100 identical to those of FIGS. 1-9.

As described above, both the first wall 120 and the second wall 122 (dimensionally and geometrically identical) of the collector 1 of FIGS. 14 and 15 are designed to be pressed during washing and discharge against the skin between upper lip and nasal pyramid of the user, allowing positioning of the respective first interface 1240 set up with the syringe 36, and therefore the respective nasal nozzle 34, indifferently either facing the right-hand nasal vestibule or the left-hand nasal vestibule, or in sequence, by simply rotating the collector 1 by 180°.

Figure 18:
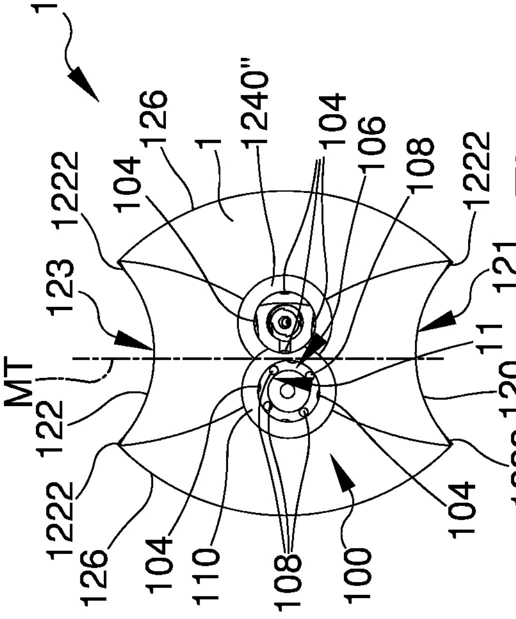
FIG. 18 is a view from below of FIGS. 17*a* and 17*b*, without details which are concealed for the sake of clarity.
Figure 17B:
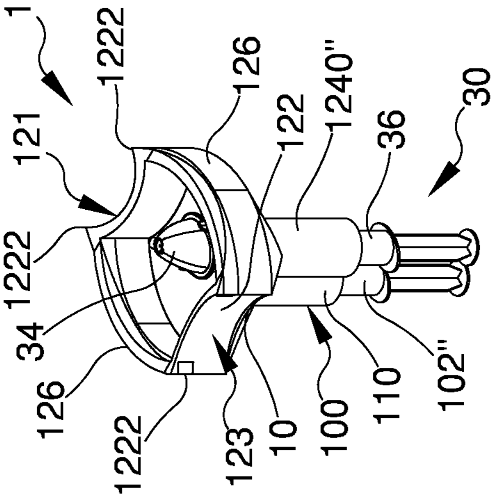
FIG. 17*b* is a three-dimensional schematic view of FIG. 16 on a reduced scale and in a second operating condition.
Figure 17A:
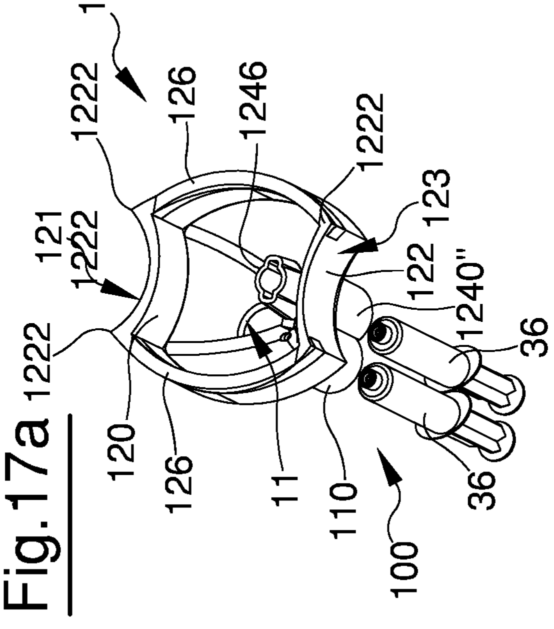
FIG. 17*a* is a three-dimensional schematic view of FIG. 16 on an enlarged scale.
Figure 20:
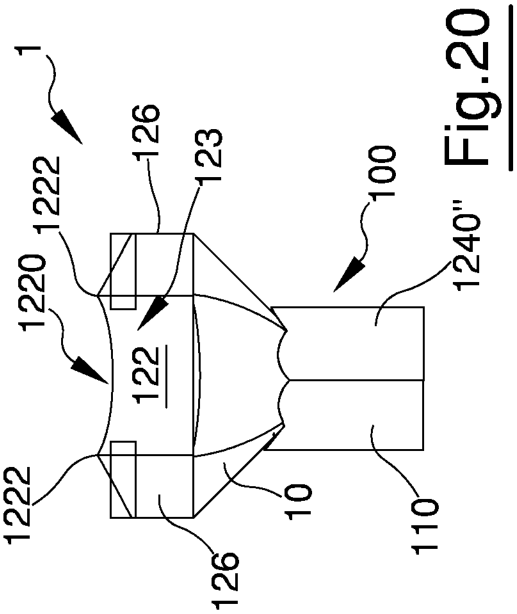
FIG. 20 is a rear elevation view of FIG. 18.
Figure 19:
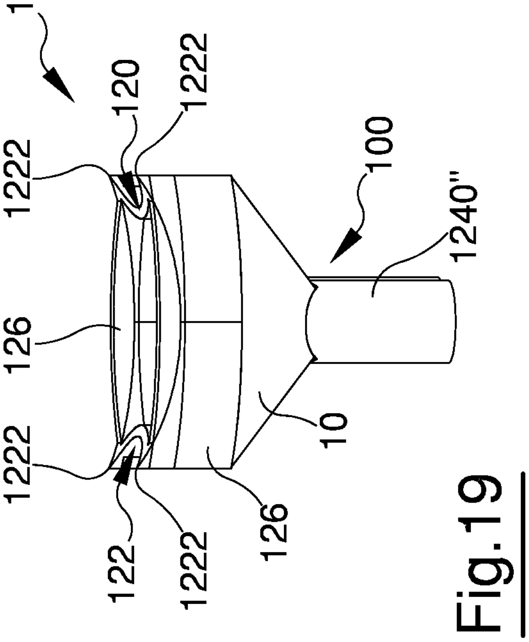
FIG. 19 is a side elevation view of FIG. 18.

With reference to FIGS. 16-20 a collector 1 is illustrated which is symmetrical relative to the transverse centreline plane MT and has the first wall 120 and the second wall 122 connected at the sides 124 by identical opposite lateral walls 126, also shaped symmetrically relative to the centreline plane MT of the first body 10. In particular, in this case the coupling members 100 have been modified and the first cylindrical portion 130 which is positioned below the annular edge 12 is missing so that the first body 10 is visible; furthermore, the first interface 1240 and the second interface 1240' are replaced by a third interface 1240" carried at the bottom by the first body 10 parallel to the centreline plane MT alongside the outlet 11, to which a duct 110 corresponds, forming part of the modified coupling members 100. Also in this case, the third interface 1240" is pre-arranged to house the syringe 36, but the respective outlet nozzle protrudes inside the first body 10 to support the nasal nozzle 34 directly or through an extension 1244 carried by the third interface 1240" through a respective mouth 1246 (FIG. 17*a*) inside the first body 10. The outlet duct 110 and the third interface 1240" share preferably but not exclusively a portion of the respective outer mantles, globally defining an “8”-shaped body in cross section (FIG. 18). It can be easily seen that the collector 1 according to the FIGS. 16-20 can house inside the respective duct 110 either a second syringe 36 as in FIGS. 16 and 17*a*, or a test tube 102" as in FIG. 17*b*, without modifying the scope of the present invention. Also in this case, to improve the capacity to retain the vials or the test tubes 102", and discharge the air contained in them, the duct 110 and the third interface 1240" have at least one longitudinal rib 104 and at least one abutment 108, already described with reference to FIG. 5 of the embodiment of the collector 1 shown in FIGS. 1-9. In FIG. 18 uniformly distributed ribs 4 protrude from the inner mantle of the duct 110 and from the inner mantle of the third interface 1240" and the abutment 106 has the same number of elevations 108 offset relative to the ribs 104, without said characteristic representing a limit to the scope of the present invention.

As described above, both the first wall 120 and the second wall 122 (dimensionally and geometrically identical) are designed to be pressed against the skin between the upper lip and nasal pyramid of a user, allowing positioning of the third interface 1240" set up with the syringe 36, and therefore the nasal nozzle 34, indifferently either facing the right-hand nasal vestibule or the left-hand nasal vestibule, or in sequence, by simply rotating the collector 1 by 180°.

Figure 22:
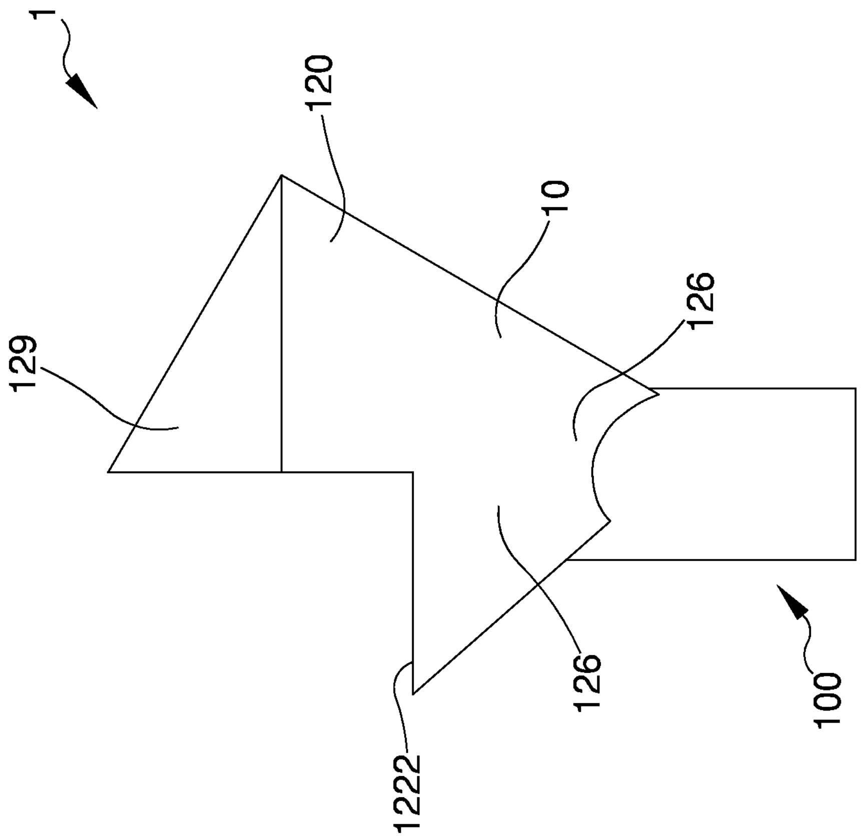
FIG. 22 is a side elevation view of FIG. 21.
Figure 21:
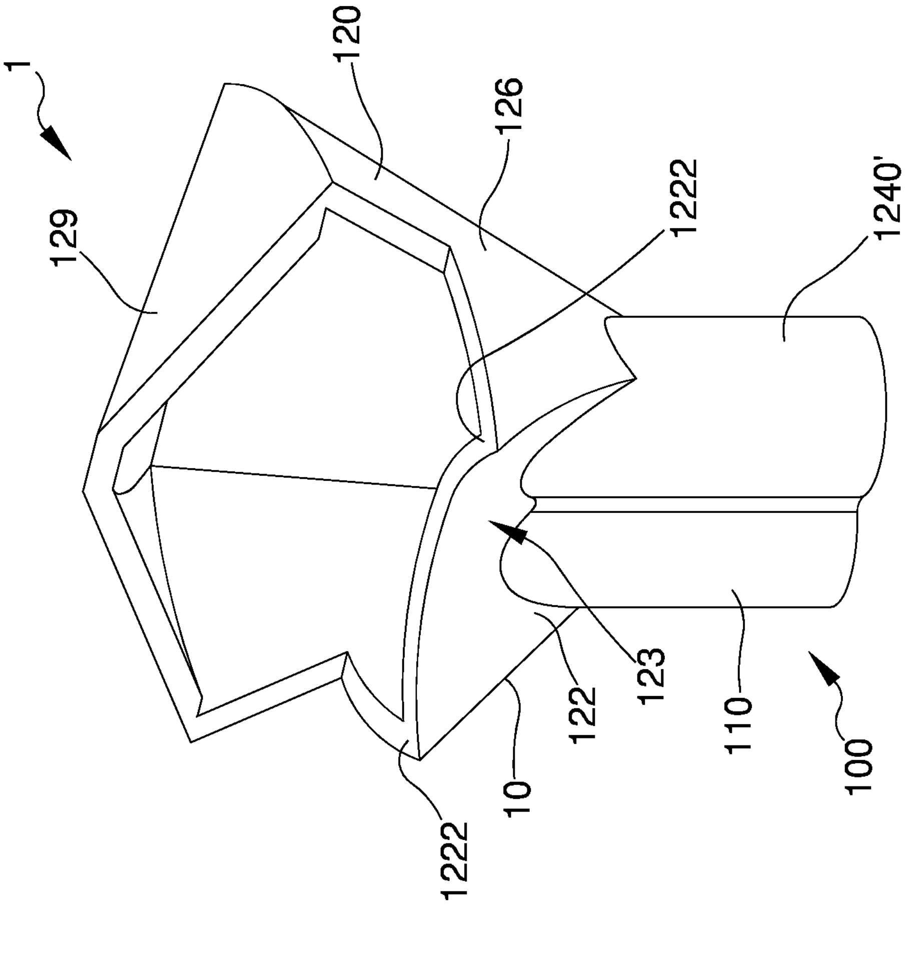
FIG. 21 is a three-dimensional schematic view of a sixth preferred embodiment of FIG. 1.
Figure 24:
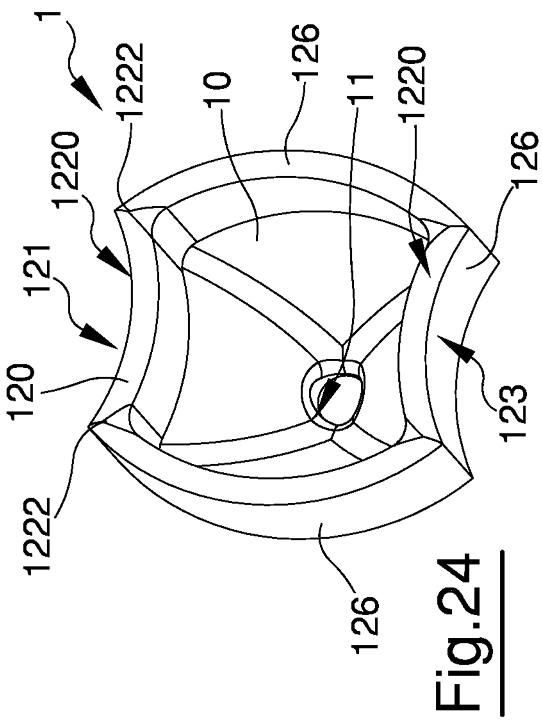
FIG. 24 is a three-dimensional schematic view from another point of view of FIG. 23.
Figure 26:
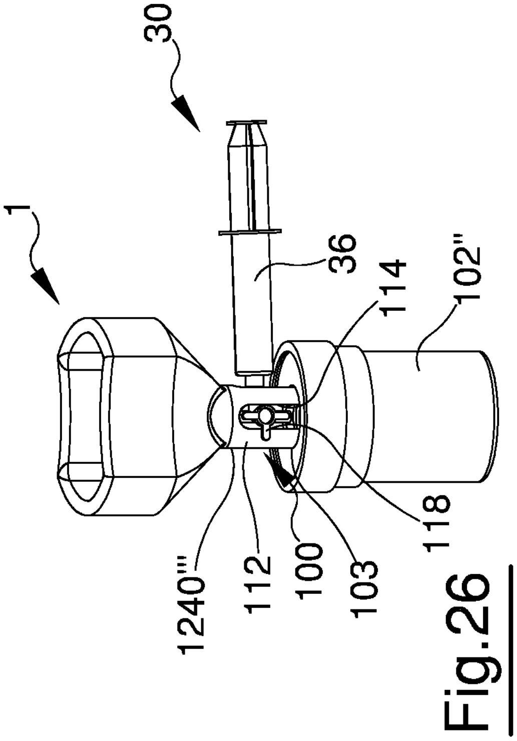
FIG. 26 is a rear three-dimensional schematic view of FIG. 23 in a second operating condition.
Figure 23:
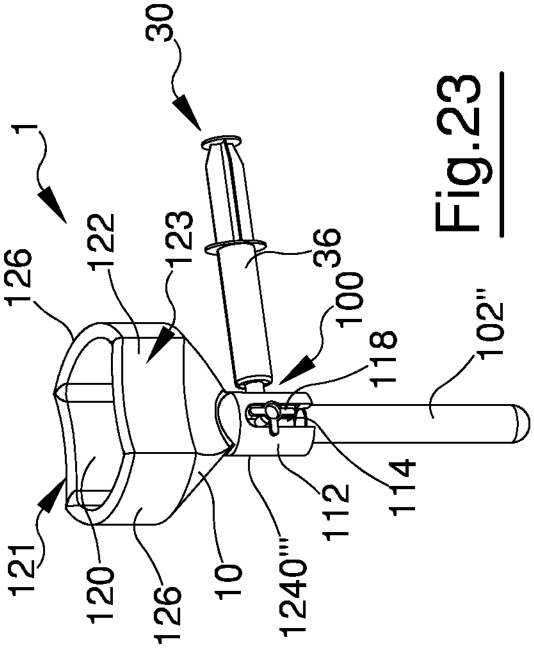
FIG. 23 is a three-dimensional schematic view of a seventh preferred embodiment of FIG. 1 in a first operating condition.
Figure 25:
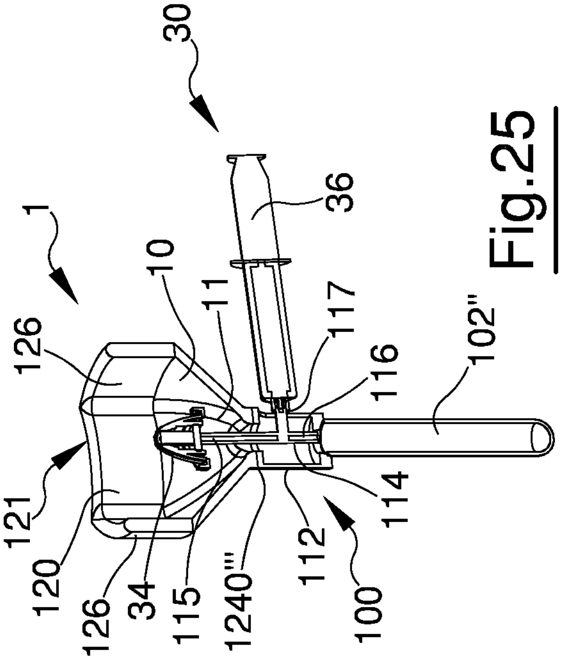
FIG. 25 is a longitudinal section view of FIG. 23 according to a transverse centreline plane.

With reference to FIGS. 21 and 22 the collector 1 can be modified relative to the collector 1 of FIGS. 16-20 with particular reference to the respective first wall 120, which can be raised and present a cover 129 similar to the cover of FIGS. 10 and 11, where the first wall 120 can be flat, concave or convex relative to the first body 10, without modifying the scope of the present invention.

Differently, the collector 1 can be modified with particular reference to FIGS. 23-26 maintaining the first body 10 visible, modifying the coupling members 100 and defining a unique route via which the washing liquid can be delivered and discharged once the nasal cavity has been sprayed.

In particular, said route is implemented in the hole that defines the outlet 11. For orderly operation, the first body 10 carries at the bottom, around the hole of the outlet 11, a fourth interface 1240''' provided with a housing member 112 having longitudinal windows and pre-arranged to house a two-way hydraulic selector 114 (FIG. 25) provided with first and second aligned ducts 115 and 116 and a duct 117 transverse to the other two, in addition to a switching tap 118. The first aligned duct 115 engages, in use, the hole of the outlet 11 and carries the nasal nozzle 34 inside the first body 10. The other aligned duct 116 engages the housing member 112 and, inside it, can house the neck of a test tube 102', supported by the lower edge of the housing member 112, which is part of the housing members 100 modified for this version of the collector 1. The remaining transverse duct 117 is engaged by the outlet nozzle of a syringe 36. The tap 118 is designed to selectively determine the connection between the first aligned duct 115 and the transverse duct 117 (condition of delivery of washing liquid through the nasal nozzle 34) and the connection between the first aligned duct 115 and the second aligned duct 116 (outlet condition) without requiring the nasal nozzle 34 to be moved away from the edge of the nostril sprayed with the liquid. Naturally, operation of the device will be identical if the test tube 102" is replaced by a vial 102', appropriately provided with an adapter 103 which stably connects it to the outside of the housing member 112.

Also in this case, both the first wall 120 and the second wall 122 (dimensionally and geometrically identical) are designed to be pressed against the skin between the upper lip and nasal pyramid of the user, allowing positioning of the syringe 36, and therefore the corresponding nasal nozzle 34, indifferently either facing the right-hand nasal vestibule or the left-hand nasal vestibule, or in sequence, by simply rotating the collector 1 by 180°.

Figure 28:
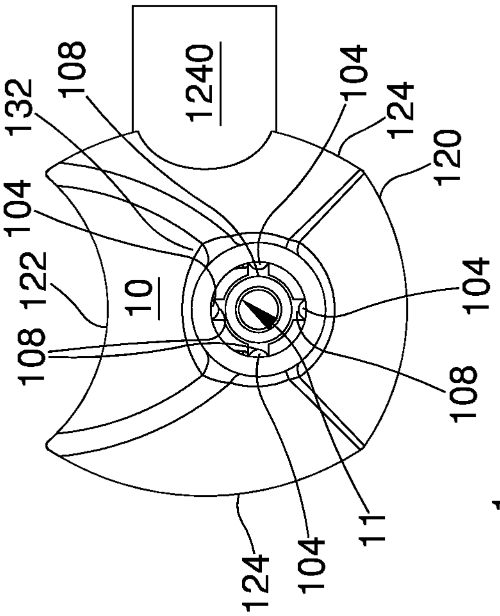
FIG. 28 is a view from below of FIG. 27.
Figure 29:
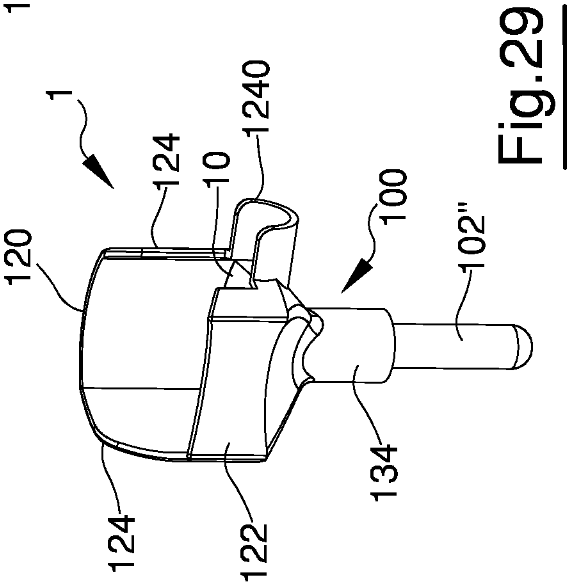
FIG. 29 is a three-dimensional schematic view on a reduced scale of FIG. 27 in a condition of use.
Figure 27:
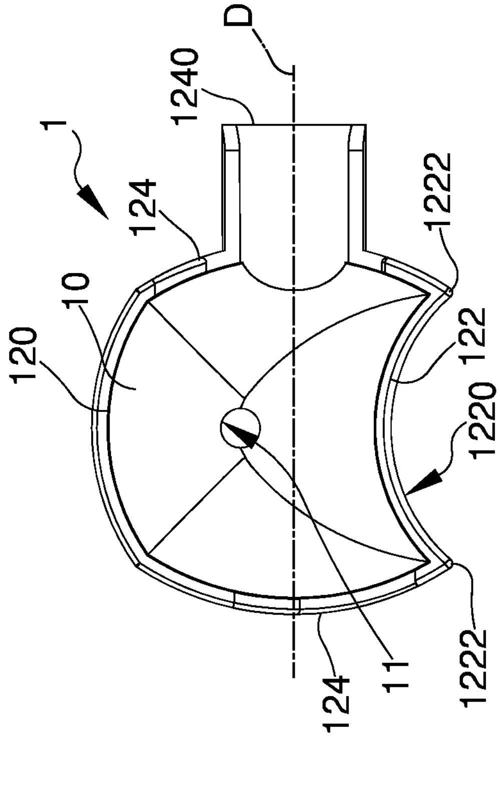
FIG. 27 is a plan view of an eighth preferred embodiment of FIG. 1.

With reference to FIGS. 27-29, a further embodiment of the present invention is illustrated, which can be considered a variation of the version described with reference to FIGS. 1-9, in which the liquid is delivered by a nasal nozzle 34 supplied by a syringe 102" housed inside the first interface 1240, the only interface present in this embodiment. As can be seen in FIG. 28, and more distinctly in FIG. 9, the coupling members 100 comprise exclusively the second hooking portion 134 to house a test tube 102" below the outlet 11. Therefore, once the washing has been carried out, the liquid containing the removed nasal secretion flows inside the first body 10 and from here to the test tube 102" housed inside the second hooking portion 134 through the outlet 11.

Figure 31:
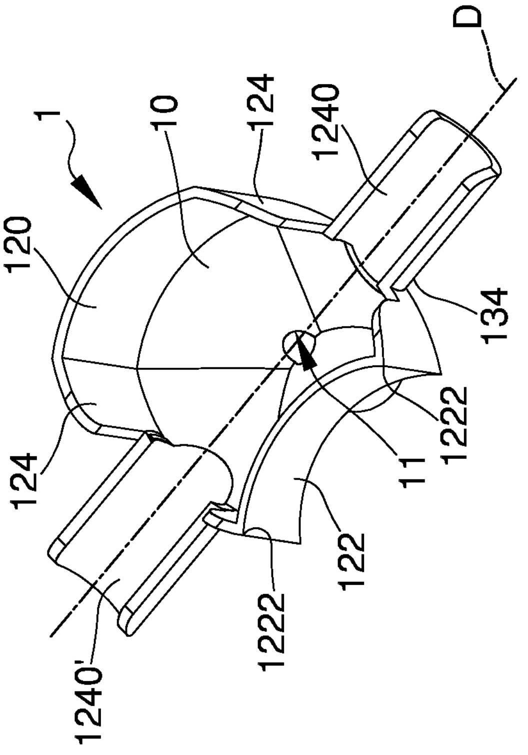
FIG. 31 is a three-dimensional schematic view of FIG. 30.
Figure 30:
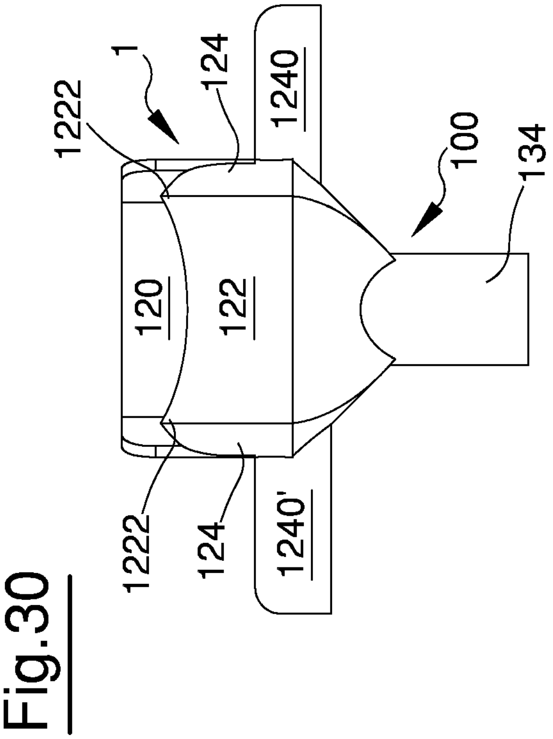
FIG. 30 is a side elevation view of a ninth preferred embodiment of FIG. 1.
Figure 32:
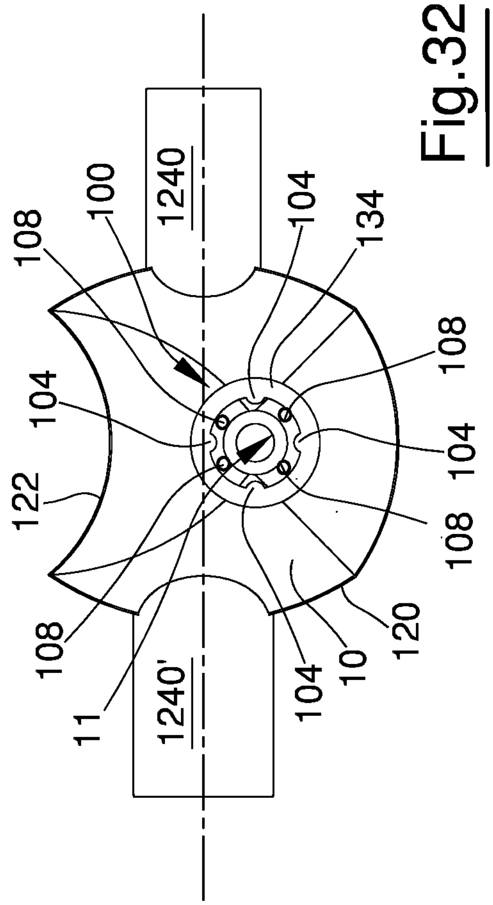
FIG. 32 is a view from below of FIG. 30.

With reference to FIGS. 30-32 the collector of FIGS. 27-29 is provided with two interfaces 1240 and 1240' as in FIGS. 12 and 13.

Figure 34:
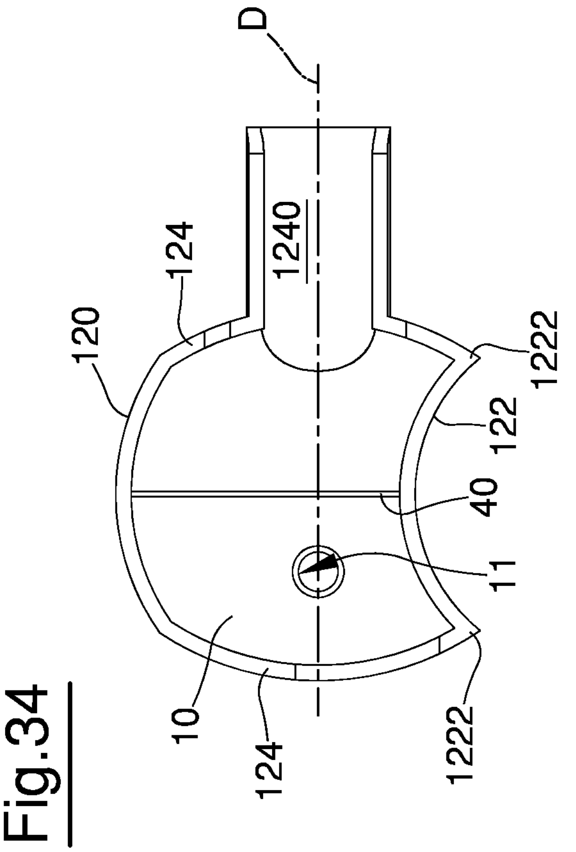
FIG. 34 is a plan view of FIG. 33.
Figure 35:
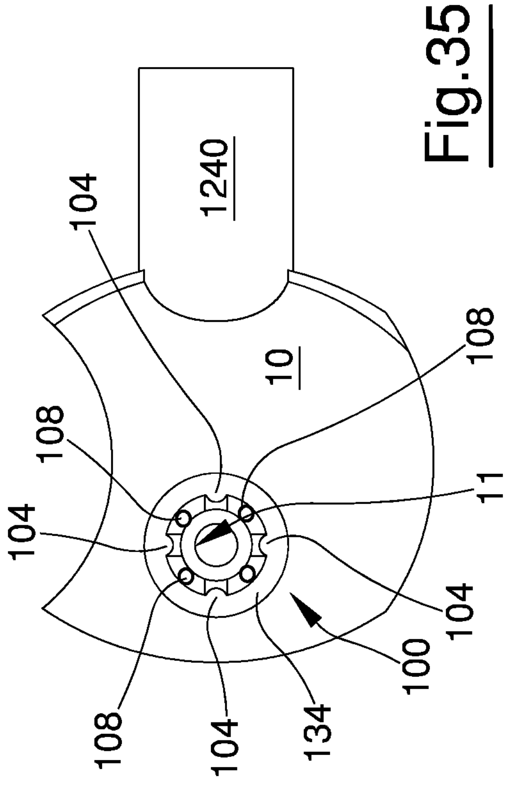
FIG. 35 is a view from below of FIG. 33.
Figure 33:
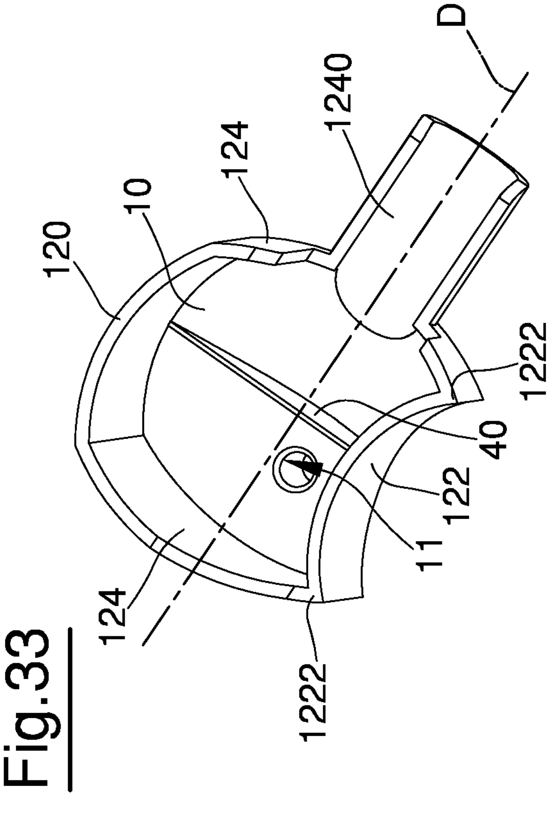
FIG. 33 is a three-dimensional schematic view of a tenth embodiment of FIG. 1.

FIGS. 33-35 show a modified version of the collector 1 illustrated in FIGS. 27-29, where the first body 10, and the first front wall 120 and the second rear wall 122, is cut in two by a partition 40 which divides the volume delimited by the first body 10 into two parts and, in turn, is delimited at the top by a rectilinear edge 41 which connects two portions of the annular edge 12 of the first body 10, resulting transverse to the given direction D, therefore horizontal when the collector 1 is arranged with the respective second hooking portion 134 oriented vertically. The division determined by the partition 40 inside the first body 10 requires the outlet 11 to be moved laterally relative to the partition 40, on the side opposite the interface 1240, and also the second hooking portion 134 for obvious construction reasons.

Figure 37:
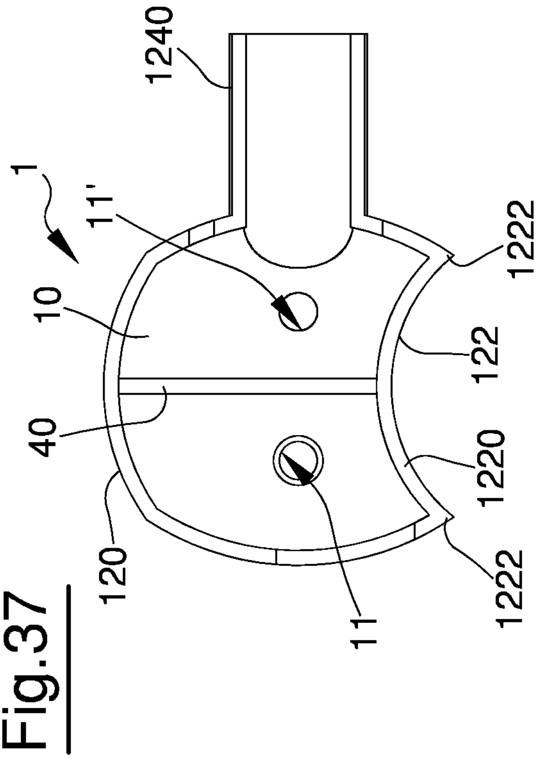
FIG. 37 is a plan view on an enlarged scale of FIG. 36.
Figure 38:
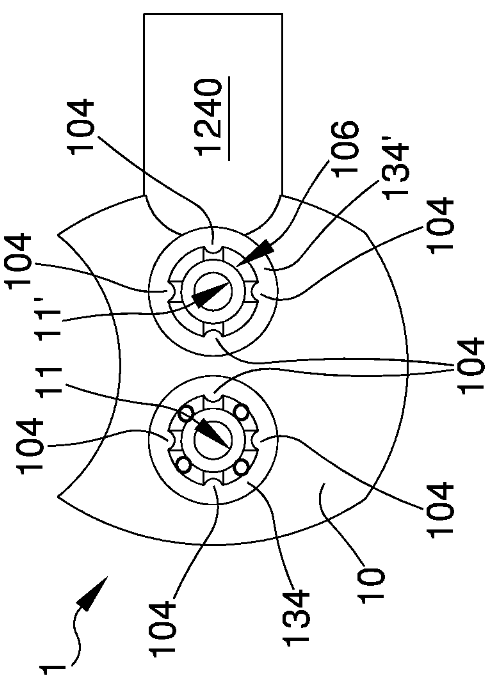
FIG. 38 is a view from below on an enlarged scale of FIG. 36 without details which are concealed for the sake of clarity.
Figure 36:
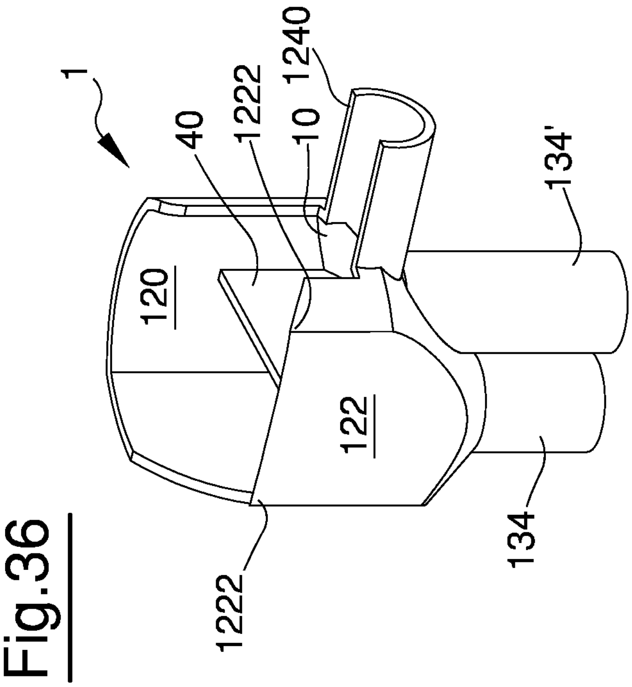
FIG. 36 is a three-dimensional schematic view of an eleventh embodiment of the present invention.

The FIGS. 36-38 show a modified version of the collector 1 illustrated in FIGS. 33-34 in which the outlet 11 is combined, on the side opposite the partition 40, with an outlet hole 11' which opens to a further second hooking portion 134' for a further test tube 102", which can be used to collect the liquid that could flow out of the free nostril from the nasal nozzle 34 once the liquid has been delivered by the syringe 36 supported by the interface 1240, if said fraction of liquid has to be collected uncontaminated in order to be then examined in some way.

Figure 40:
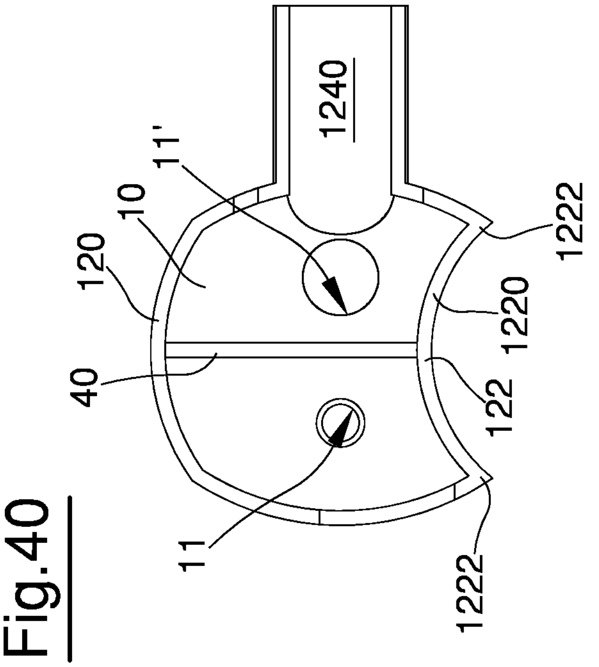
FIG. 40 is a plan view on an enlarged scale of FIG. 39.
Figure 41:
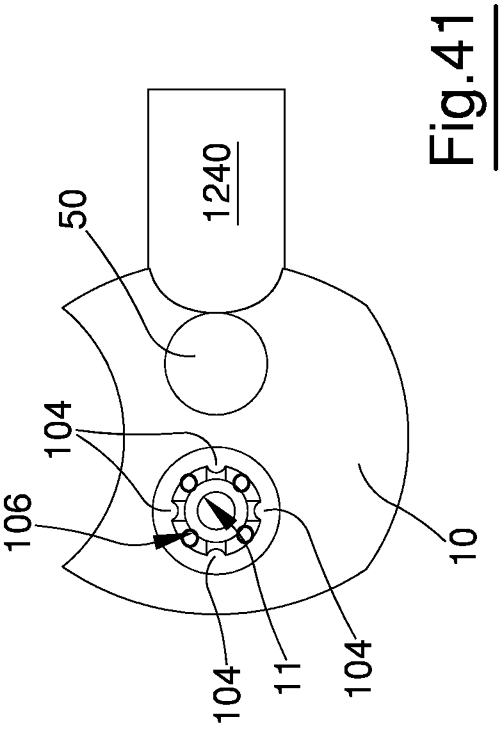
FIG. 41 is a view from below on an enlarged scale of FIG. 39 without details which are concealed for the sake of clarity.
Figure 39:
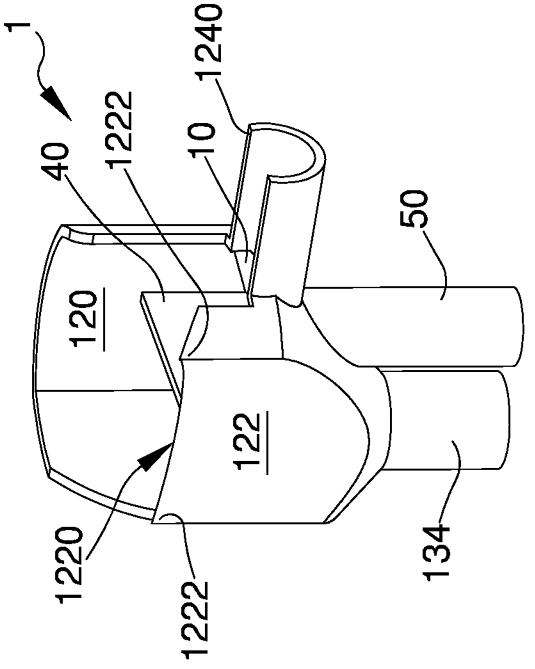
FIG. 39 is a three-dimensional schematic view of a twelfth embodiment of the present invention.

In FIGS. 39-41 a variation of the embodiment of FIGS. 36-38 is illustrated, in which the further second hooking portion 134' is replaced by a cylindrical tank 50 that can be used to collect the fraction of liquid that could flow out of the free nostril from the nasal nozzle 34 once the liquid has been delivered by the syringe 36 supported by the interface 1240. The choice to equip the collector 1 with a tank 50, which could equip any embodiment of the collector described above, is particularly useful if collection of the liquid fraction that has flowed out of the free nostril from the nasal nozzle 34 is desired but it is not of primary importance to collect it uncontaminated in a test tube, for example to then disperse it in a given environment.

Figure 43:
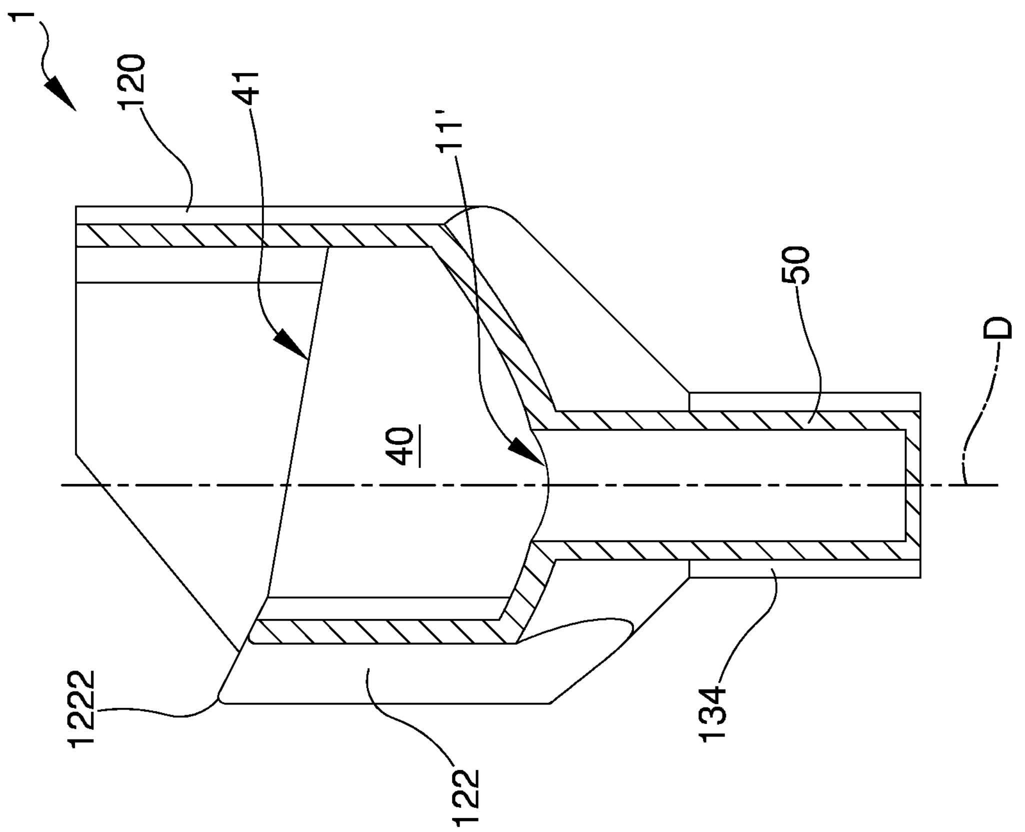
FIGS. 42 and 43 are a three-dimensional schematic view and a longitudinal sectional view respectively of a thirteenth embodiment of FIG. 1.
Figure 42:
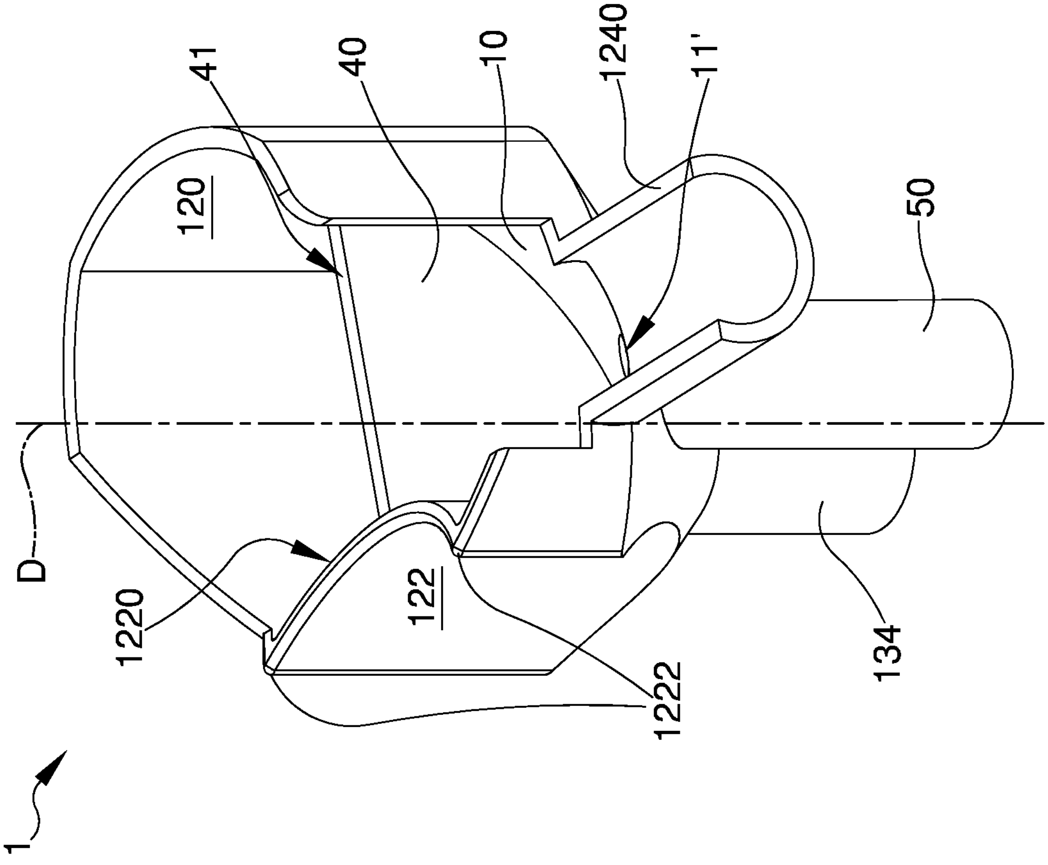
Figure 44:
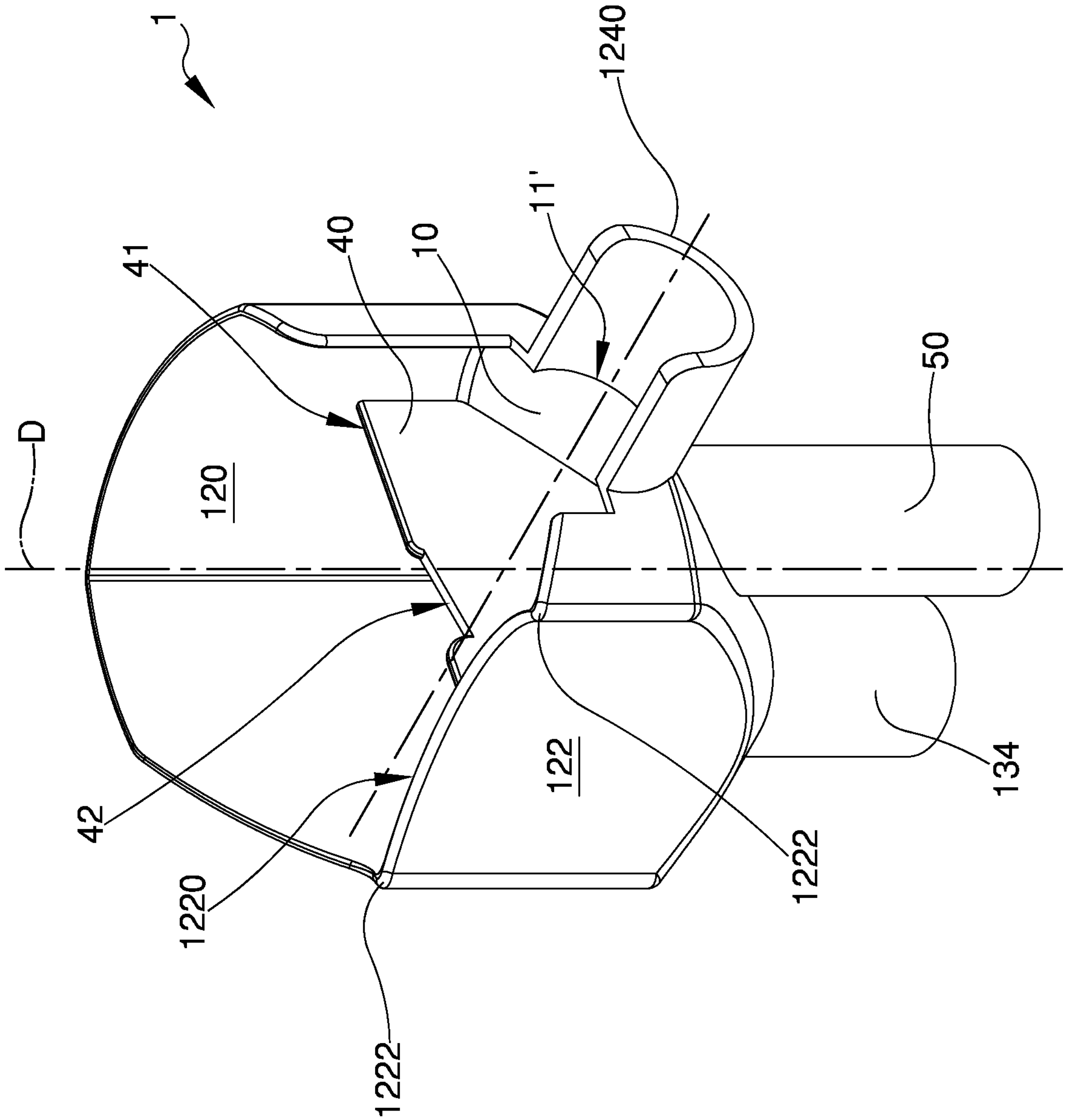
FIG. 44 is a three-dimensional schematic view of a fourteenth embodiment of FIG. 1.

In FIGS. 42 and 43 a variation of the collector 1 of FIGS. 39-41 is illustrated, in which the rectilinear edge 41 of the partition 40 is inclined downwards proceeding from the second rear wall 122 to the first front wall 120. In particular, with reference to FIG. 43, the edge 41 is inclined downwards so as to present a greater extension at the intersection with the second rear wall 122 and lesser at the intersection with the first front wall 120. In some cases, as in FIG. 44, the rectilinear edge 41 of the partition 40 has a lowered area 42 facing the interface 1240 and, in use, facing the nozzle 34 carried by the syringe 36 housed in the interface 1240, so as to allow a lateral portion of the nozzle 34 to be superimposed on the partition, to maximize the adaptability of the position of the nozzle 34 along the interface 1240 to be compatible with different user nose shapes.

Based on the above description, it can be easily seen that the collector 1 solves in a simple inexpensive manner the drawbacks typical of the state of the art illustrated above, in addition to allowing the definition of new operating protocols for sampling the nasopharyngeal/olfactory nasal secretion of numerous groups of persons to be analysed in complete safety and with a high degree of reliability, permitting the collection of nasal secretion mixed with washing liquid in an autonomous manner, excluding the risk of third party contamination and being error-proof.

At this point, it may be useful to specify that in the following claims any reference sign in brackets should not be interpreted as a limitation to the claim. The word "comprising" does not exclude the presence of other elements or phases in addition to those listed in a claim. Furthermore, the term "one", as used in this context, is defined as one or more than one. Furthermore, the use of introductory phrases like "at least one" and "one or more" in the claims should not be interpreted in the sense that the introduction of another claim element by the indefinite article "a" or "an" limits any particular claim containing said claim element introduced to the inventions that contain only one, even when said claim comprises introductory phrases "one or more" or "at least one" and indefinite articles like "a" or "an". The same applies to the use of definite articles. Unless established otherwise, terms such as "first" and "second" are used to arbitrarily distinguish the elements that said terms describe. Therefore, these terms are not necessarily intended to indicate the temporal priority or other type of priority of said elements. The simple fact that some measures are illustrated in mutually different claims does not indicate that a combination of these measures cannot be used to advantage.

The invention claimed is:

1. A collector (1) for liquids provided with a first funnel-shaped body (10) delimited at the top by an annular edge (12) and provided at the bottom with an outlet (11) for said liquids and with coupling means (100) for removable collection members (102) of said liquids from said outlet (11); said collector comprising a first front wall (120) and a second rear wall (122) carried in a hydraulically sealed manner by said annular edge (12) between two sides (124) of said first body (10) and mutually facing one another: said second rear wall (122) being delimited at the top by a concave curved segment (1220) shaped for shape coupling, in use, with an anatomic facial portion arranged between a user's top lip and nose: the said collector comprising at least one interface (1240)(1240')(1240") elongated according to a given direction (D) arranged between said first front wall (120) and said second rear wall (122); said at least one interface (1240)(1240')(1240") being pre-arranged to house supply means (30) designed to distribute the liquid in a direction opposite to said outlet (11) between said first wall (120) and said second wall (122) through a nasal nozzle (34); characterized in that said first front wall (120) and said second rear wall (122) are separated in at least one first side (124A) of said two sides (124) creating a first opening (128)(128') above said first body (10): a first interface (1240) that actuates said at least one interface (1240) being carried by said first side (124A) along said given direction (D) through said first opening (128).

2. The collector according to claim 1, characterised in that said first front wall (120) and said second rear wall (122) are symmetrically shaped relative to a centreline plane (MT) that transversally cuts said first body (10); said curved segment (1220) being laterally delimited by two raised angle portions (1222) arranged symmetrically so as to laterally delimit the nostrils of said nose.

3. The collector according to claim 1, characterised in that said first interface (1240) has a retention element (1242) for said liquid supply means (30) at the corresponding said first side (124A).

4. The collector according to claim 3, characterised in that said liquid supply means (30) comprise a syringe (36) provided with one said nasal nozzle (34) carried longitudinally or transversely by said syringe (36); said retention element (1242) comprising an at least partially cylindrical projecting part (1242) having an angular width greater than 180° and arranged at the connection between said first interface (1240) and said first side (124A).

5. The collector according to claim 4, characterised in that said first front wall (120) and said second rear wall (122) are identical and have the respective concavities (121)(123) facing the side opposite to said outlet (11).

6. The collector according to claim 4, characterised in that said first front wall (120) extends from said annular edge (12) by a greater amount than said second rear wall (122).

7. The collector according to claim 6, characterised in that said first front wall (120) carries at the top a tapered shaped cover member (129) shaped for containing a nasal pyramid starting from a relative root.

8. The collector according to claim 1, characterised in that said first front wall (120) and said second rear wall (122) are separated in a second side (124B) of said two sides (124) creating a second opening (128') identical or geometrically similar and opposite to said first opening (128); a second interface (1240') that actuates said at least one interface (1240) being carried by said second side (124B) aligned with said first interface (1240) and sized in a different yet geometrically similar manner.

9. The collector according to claim 1, characterised in that said first front wall (120) and said second rear wall (122) are connected to said two sides (124) of said first body (10) by respective walls (126) being shaped symmetrically opposite relative to said centreline plane (MT).

10. The collector according to claim 9, characterised in that said first front wall (120) and said second rear wall (122) have the respective concavities (121)(123) facing the side opposite to said outlet (11).

11. The collector according to claim 1, characterised in that said coupling means (100) comprise in combination, or alternatively, a first cylindrical portion (130) that peripherally delimits said outlet (11) and terminates with a first hooking portion (132), shaped to be coupled in a hydraulically sealed manner with an upper edge of a collection vial (102') for a liquid to be analysed, and a second cylindrical hooking portion (134) coaxial to said outlet (11) shaped to house a hydraulically sealed test tube (102").

12. The collector according to claim 9, characterised in that a third interface (1240") that actuates said at least one interface (1240) is carried at the bottom by said first body (10) alongside said outlet (11), extends parallel to said centreline plane (MT) and transversely to said annular edge (12) and being arranged to house a syringe (36) of said supply means (30) with said outlet nozzle that protrudes inside said first body (10) to support said nasal nozzle (34) directly or through an extension (1244) carried by said third interface (1240") inside said first body (10).

13. The collector according to claim 9, characterised in that a fourth interface (1240'") that actuates said at least one interface (1240) comprises a housing member (112) carried at the bottom by said first visible body (10); said housing member (112) being prearranged to receive a two-way hydraulic selector (114) provided with a first duct and with a second duct (115)(116) aligned with one another and with a duct (117) transversal to the other two, as well as a switching tap (118); said first aligned duct (115) engaging, in use, said outlet (11) and carrying said nasal nozzle (34) inside the first body (10); said second aligned duct (116) engaging a test tube (102") or a vial (102') selectively supported at the bottom by said housing member (112); said transverse duct (117) being engaged by an outlet nozzle of said syringe (36); said tap (118) being designed to determine selectively the connection between said first aligned duct (115) and said transverse duct (117) and the connection between said first aligned duct (115) and said second aligned duct (116).

* * * * *